US009023004B2

(12) United States Patent
Kuramochi

(10) Patent No.: US 9,023,004 B2
(45) Date of Patent: May 5, 2015

(54) ABSORPTIVE ARTICLE

(75) Inventor: Mihoko Kuramochi, Sakura (JP)

(73) Assignee: Daio Paper Corporation, Ehime (JP)

( * ) Notice: Subject to any disclaimer, the term of this patent is extended or adjusted under 35 U.S.C. 154(b) by 0 days.

(21) Appl. No.: 13/519,099

(22) PCT Filed: Dec. 22, 2010

(86) PCT No.: PCT/JP2010/073128
§ 371 (c)(1),
(2), (4) Date: Jun. 25, 2012

(87) PCT Pub. No.: WO2011/078222
PCT Pub. Date: Jun. 30, 2011

(65) Prior Publication Data
US 2012/0265162 A1    Oct. 18, 2012

(30) Foreign Application Priority Data

Dec. 25, 2009    (JP) .................................. 2009-294477

(51) Int. Cl.
*A61F 13/475*    (2006.01)
*A61F 13/15*    (2006.01)
*A61F 13/00*    (2006.01)
*A61F 13/47*    (2006.01)

(52) U.S. Cl.
CPC ......... *A61F 13/4704* (2013.01); *A61F 13/4758* (2013.01)

(58) Field of Classification Search
CPC ........ A61F 13/00; A61F 14/15; A61F 13/475
USPC ................................... 604/383, 385.101, 358
See application file for complete search history.

(56) References Cited

U.S. PATENT DOCUMENTS

2006/0058761 A1 * 3/2006 Kudo et al. ................... 604/380
2011/0130737 A1   6/2011 Sagisaka et al.

FOREIGN PATENT DOCUMENTS

| JP | 2003-033397 | 2/2003 |
| JP | 2007-195665 | 8/2007 |
| JP | 2009-082480 | 4/2009 |
| JP | 2009082480 A * | 4/2009 |
| JP | 2009-273724 | 11/2009 |
| WO | WO-2009/139248 | 11/2009 |

* cited by examiner

*Primary Examiner* — Tatyana Zalukaeva
*Assistant Examiner* — Sara Sass
(74) *Attorney, Agent, or Firm* — Jordan and Hamburg LLP

(57) ABSTRACT

In an absorptive article, fitting performance is improved by following the shape and movement of a body, and wrinkles in a blood discharge opening corresponding portion are eliminated and wearing comfort is improved by separating movement of each part from each other so that the blood discharge opening corresponding portion is not affected.

3 Claims, 5 Drawing Sheets

ABSORPTIVE ARTICLE

BACKGROUND OF THE INVENTION

The present invention relates to an absorptive article such as a sanitary napkin, a pantiliner, an incontinence pad and the like for absorbing menstrual blood, vaginal discharge and the like, or more particularly to an absorptive article which fits the shape and movement of a body, eliminates wrinkles and is more comfortable to wear.

Known absorptive articles, such as a sanitary napkin, a pantiliner, an incontinence pad and the like, include those interposing an absorptive element containing an absorbing body made of a cotton-state pulp between an impermeable back-surface sheet such as a polyethylene sheet, a polyethylene laminate unwoven cloth or the like and a permeable front-surface sheet such as a nonwoven cloth, a permeable plastic sheet or the like.

Various improvements have been made for this type of absorptive article, and in order to improve comfort of wear and fit, those provided with an emboss having a predetermined shape from the front surface side of the permeable front-surface sheet are known.

For example, Japanese Unexamined Patent Application Publication No. 2009-82480 discloses, as illustrated in FIG. 5, a sanitary napkin 50 in which a front-surface sheet 51, an absorbing core 52, and a back-surface sheet 53 are laminated in this order. A first emboss 54 forming a line going in the front-and-rear direction is provided on both sides of a center portion in the front-and-rear direction of the absorbing core 52 from above the front-surface sheet 51, and a second emboss 55 forming a straight line starting from the center portion in the width direction as a base end and extending outwardly to both sides in the front-and-rear direction, respectively, from this base end is provided on at least one of a front end portion and a rear end portion of the absorbing core 52 from above the front-surface sheet 51. According to the sanitary napkin 50 as above, if a pressure P going inward from the both sides in the width direction is applied when the sanitary napkin is being worn, upper layer portions of the front-surface sheet 51 and the absorbing core 52 are brought closer to a center line C in the width direction (direction indicated by reference character F) from the second emboss 55. As a result, particularly at least the surface shape of a center portion T in the width direction on the end portion in the front-and-rear direction of the sanitary napkin 50 protrudes to the wearer side, and the fitting performance for the wearer is considered to be improved.

Japanese Unexamined Patent Application Publication No. 2007-195665 discloses an absorptive article 60, as illustrated in FIG. 6, in which left and right grooves 61 and 62 are separated from both a front groove 63 and a rear groove 64, and front end portions 61A and 62A of the left and right grooves are located closer to the front in the longitudinal direction than a rear end portion 63A of the front groove, while rear end portions 61B and 62B of the left and right grooves are located closer to the back in the longitudinal direction than a front end portion 64A of the rear groove. According to such absorptive article 60, if an area surrounded by the left and right grooves 61 and 62 is subjected to a compression force inwardly in the width direction from right and left when the absorptive article is being worn, the article is stably raised toward the wearer by forming a substantially V-shaped folding line 65 formed of lines virtually extended from the left and right grooves 61 and 62 to the front end portion and a substantially V-shaped folding line 66 formed of lines virtually extended from the left and right grooves 61 and 62 to the rear end portion as flexible axes, thus fitting the excretion portion of the wearer.

SUMMARY OF INVENTION

The shape of a female body is very different depending on the portion, such as a recess is formed in a blood discharge opening portion and a perineal region, respectively, in the center part of the body, the front side from this center part is rounded around pubes, and a valley in the buttocks is formed in the back side from the center part. When movement of the body is examined while walking, the center part of the body rarely moves since it is a portion close to the axis of the body, the back side from this center part has the largest movement since the buttocks vertically move during walking, and the front side from the center part has relatively less movement than the back side but some movement is generated therein. As described above, the shape of the body and the movement of the body are very different depending on each portion, and thus, it is important that the absorptive article is made deformable so as to adapt to the shape and movement of the body, while the movement of each portion of the absorptive article is not allowed to interlock with the other portions or particularly the center part corresponding to the blood discharge opening portion in order to improve fitting performance and wearing comfort of the absorptive article.

However, with the absorptive articles 50 and 60 in the above-described prior art documents, despite the fact that the shape and movement of the body are different between the front side and the back side as described above, the embosses are provided substantially symmetrically in the longitudinal direction. If the front side portion and the back side portion are formed so as to be easily deformed to follow the valley in the buttocks, the fitting performance on the front side portion is lost, the movement of the front side portion cannot be followed, and front leakage along the curve around the pubes can easily occur, while if the front side portion and the back side portion are formed so as to be easily deformed to follow the curve around the pubes, to the contrary the fitting performance on the back side portion is lost, the movement of the buttocks cannot be followed, and rear leakage down the valley of the buttocks can easily occur. Moreover, with particularly strenuous movement of the buttocks, wrinkles can be generated even in the center part corresponding to the blood discharge opening portion or close contact with the blood discharge opening portion or perineal region may be lost, which might deteriorate the wearing comfort.

Moreover, if the portion surrounded by the pair of left and right embosses 54 and 54 (61 and 62) is subjected to a compression force inward in the width direction from the right and left, the center of this portion is raised since the emboss is substantially symmetrical in the longitudinal direction in the center part corresponding to the blood discharge opening portion. However, the shape of the blood discharge opening portion of a woman is complicated, and even if a portion of the absorptive articles can be made to substantially fit the periphery of the blood discharge opening portion of a woman, since the perineal region from the vaginal opening to the periphery of the anus on the back side forms a three-dimensional shape in the small recessed state, the aforementioned portion of the absorptive article cannot fit this perineal region. Therefore, menstrual blood or the like that cannot be absorbed in the periphery of the blood discharge opening is not absorbed in the perineal region, either, and might leak to the rear.

A main object of the present invention is to provide an absorptive article in which the fitting performance is improved by following the shape and movement of the body and wrinkles in a blood discharge opening corresponding portion are eliminated to improve the wearing comfort by separating movement of each part from each other so that the blood discharge opening corresponding portion is not affected.

According to a principal aspect of the present invention, in order to solve the above problems, an absorptive article is provided in which an absorbing element is interposed between a permeable front-surface sheet and an impermeable back-surface sheet, a pair of blood discharge opening corresponding portion embosses each having an arc-shaped curve in the substantially longitudinal direction of the absorptive article and being formed on a portion of the absorptive article which, when worn, corresponds to a blood discharge opening portion and a perineal region of the wearer, each of the embosses being located on a respective side of a longitudinal center line of the absorptive article and having a center of curvature on the opposite side of the center line, a front portion emboss in the substantially width direction of the absorptive article is formed on the front portion of the absorptive article with a separation distance provided in the longitudinal direction of the absorptive article from the blood discharge opening corresponding portion, and a back portion emboss having a substantially inverted V-shape gradually expanding rearward to both sides from a position on the longitudinal center line is formed on the back portion with a separation distance provided in the longitudinal direction of the absorptive article from the blood discharge opening corresponding portion; and the pair of right and left blood discharge opening corresponding portion embosses each have a front end portion and a rear end portion, and a separation width between the rear end portions is set smaller than the separation width between the front end portions.

In the above-described invention, the embosses for facilitating deformation to adapt to the shape and movement of each part of the body are formed on the portion corresponding to the blood discharge opening portion and the perineal region of the wearer, on the front portion with the separation distance provided in the longitudinal direction of the absorptive article from the blood discharge opening corresponding portion, and on the back portion located on the back with the separation distance provided in the longitudinal direction of the absorptive article from the blood discharge opening corresponding portion,.

Specifically, on the blood discharge opening corresponding portion, the blood discharge opening corresponding portion embosses having the arc-shaped curve in the substantially longitudinal direction of the absorptive article and having the center of curvature on the longitudinal center line are formed, respectively, on the both sides of the longitudinal center line. Particularly, in the present invention, the front end portions and the rear end portions in the pair of right and left blood discharge opening corresponding portion embosses are provided separately from each other on the both sides of the longitudinal center line, respectively, and the separation distance between the rear end portions is set smaller than the separation distance between the front end portions. Therefore, the front in the portion surrounded by the blood discharge opening corresponding portion embosses is raised to the front surface side in a relatively wide range in the width direction by a pressure inward from the both sides in the width direction from the femora, and thus, the front suitably fits the blood discharge opening portion. Moreover, since the back is raised to the front surface side within a relatively narrow range in the width direction, the back suitably fits the perineal region. Moreover, since the front portion emboss in the substantially width direction of the absorptive article is formed on the front portion, the front portion can easily deform along the curve around the pubes with the front portion emboss as the flexible axis. Furthermore, since the back portion emboss having the substantially inverted V-shape gradually expanding rearward to both sides from the position on the longitudinal center line is formed on the back portion, the back portion can easily deform along the valley of the buttocks with the back portion emboss as the flexible axis. Therefore, since the article is deformed to conform to the shape of each part of the body, fitting performance is improved, and leakage of menstrual blood or the like is reliably prevented.

Each of the blood discharge opening corresponding portion, the front portion, and the back portion is deformed so as to fit the body as described above and a discontinuous zone of the emboss line is formed between the blood discharge opening corresponding portion and the front portion as well as the back portion, respectively. Therefore, this discontinuous zone functions as a separating zone which separates movement of the front portion from that of the back portion and relieves potential influence on the blood discharge opening corresponding portion, the fitting performance of the blood discharge opening corresponding portion to the body is stably maintained regardless of the movements of the front portion and the back portion, wrinkles in the blood discharge opening corresponding portion are eliminated, and wearing comfort is improved.

When the right and left legs are moved back and forth alternately as in walking, the front portion and the back portion are interlocked with the movements of the right and left legs and generate a movement like twisting deformation. However, since the center parts in the width direction of the discontinuous zones become the base ends of the twisting deformation of the front portion and the back portion and function as separating base points which separate the movement of the front portion from that of the back portion, respectively, and relieve influences to the blood discharge opening corresponding portion, deformation of the blood discharge opening corresponding portion which would be caused by interlocking with the twisting deformation of the front side portion and the back side portion and wrinkles are suppressed, and wearing comfort is improved.

In another aspect of the present invention, in the hereinabove describe inventive absorptive article the emboss lines formed on the both sides across the longitudinal center line and constituting the back portion embosses are formed such that a virtual line extended from the front end portion of the emboss line on one side to the other side across the longitudinal center line becomes substantially parallel with a tangent line of the rear end portion of the emboss line formed on the other side of the longitudinal center line of the blood discharge opening corresponding portion embosses.

In yet another aspect of the above-described invention, regarding the back portion where the movement of the body is relatively larger than that of the front side portion, in addition to the rear-end separation width being smaller than the front-end separation width of the pair of right and left blood discharge opening corresponding portion embosses, each of the emboss lines formed on both sides across the longitudinal center line and constituting the back portion embosses is formed such that the virtual line extended from the front end portion of the emboss line on one side (V-shaped top portion at the center) to the other side across the longitudinal center line and the tangent line of the rear end portion of the emboss line formed on the other side of the longitudinal center line of the blood discharge opening corresponding portion embosses become substantially parallel with each other. As a result, the back portion is deformed along the valley of the buttocks, and because wrinkles which would otherwise develop in the direction of the blood discharge opening corresponding portion from the front end portion are absorbed by the blood discharge opening corresponding portion embosses, wrinkles are no longer formed in the portions surrounded by the blood discharge opening corresponding portion embosses, and the blood discharge opening corresponding portion can be made to fit the blood discharge opening corresponding portion and the perineal region more reliably.

As a further aspect of the present invention, in the inventive absorptive article described hereinabove the front portion emboss is formed by an arc-shaped curve having a center of curvature closer to the front of the absorptive article than the front portion emboss itself and an angle formed by tangent lines of both right and left end portions is 90° or more.

In another aspect of the invention, in order to make the front portion easily deformable with the shape following the curve around the pubes of the wearer by using the front portion emboss as a flexible axis, the front portion emboss is formed of a curve having a center of curvature closer to the front of the absorptive article than the front portion emboss itself, and the angle formed by tangent lines of both right and left end portions is 90° or more.

In another aspect of the present invention in the back portion emboss, the angle formed by the emboss lines formed on both sides across the longitudinal center line is less than 90°. Thus in order to make the back portion easily deformable with the shape following the valley in the buttocks of the wearer by using the back portion emboss as a flexible axis, the back portion emboss is configured such that the angle formed by emboss lines formed on both sides across the longitudinal center line is less than 90°.

As described above in detail, according to the present invention, the fitting performance is improved by following the shape and the movement of the body, and wrinkles in the blood discharge opening corresponding portion are eliminated and wearing comfort is improved by separating movement of each part from each other so that the blood discharge opening corresponding portion is not affected.

DETAILED DESCRIPTION OF THE INVENTION

An embodiment of the present invention will be described below in detail by referring to the attached drawings.

Figure 1:
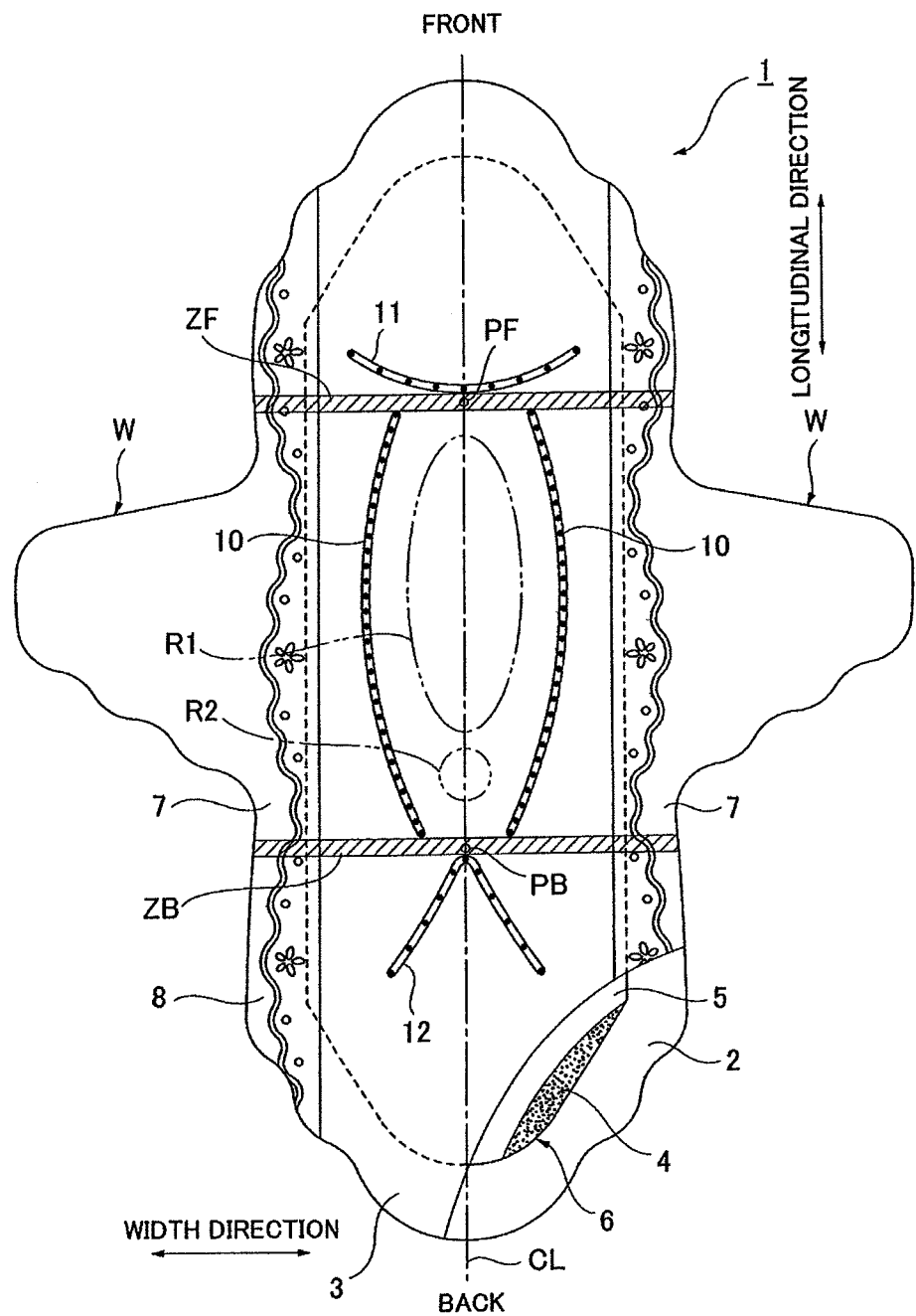
FIG. 1 is a partially broken extended diagram of a sanitary napkin 1 according to the present invention.

A sanitary napkin 1 according to the present invention includes, as illustrated in FIG. 1, an impermeable back-surface sheet 2 made of a polyethylene sheet, a polypropylene sheet or the like, a permeable front-surface sheet 3 through which menstrual blood, vaginal discharge and the like quickly permeate, an absorbing element 6 including an absorbing body 4 made of a cotton pulp or synthetic pulp interposed between sheets 2 and 3 and crepe paper 5 surrounding the absorbing body 4 for maintenance of the shape and improvement of diffusion performance of the absorbing body 4, and unwoven cloth portions 7 and 7 extending in the longitudinal direction each along respective side portions of the front surface. At the periphery of the absorbing body 4, the impermeable back-surface sheet 2 and the permeable front-surface sheet 3 are bonded by an adhesive such as hot-melt or bonding means such as heat-seal or the like. The impermeable back-surface sheet 2 and the side nonwoven cloth portions 7 protruding to the sides beyond the absorbing body 4 are bonded together on the both side edge portions thereof by an adhesive such as hot-melt or bonding means such as heat-seal or the like, and a flap portion 8 where the absorbing body 4 is not present is formed on an outer periphery.

A structure of the sanitary napkin 1 will be further described below in detail.

A sheet material having at least water shielding performance such as an olefin resin sheet including polyethylene, polypropylene and the like is used for the impermeable back-surface sheet 2. Other than the above, a laminate nonwoven cloth in which a nonwoven cloth is laminated on a polyethylene sheet or the like, a nonwoven cloth sheet in which impermeability is substantially ensured by providing a waterproof film therein (in this case, the impermeable back-surface sheet is formed of the water-proof film and the nonwoven cloth) and the like can be also used. In recent years, sheet materials with moisture permeability tend to be used from the viewpoint of prevention of a damp feeling. This water-shielding/moisture permeable sheet material is a micro-porous sheet obtained by kneading inorganic filler in a molten olefin resin such as polyethylene, polypropylene and the like and molding a sheet therefrom and then, drawing the sheet uniaxially or biaxially.

Subsequently, a porous or non-porous unwoven cloth or a porous plastic sheet is suitably used for the permeable front-surface sheet 3. As fibers constituting the nonwoven cloth, in addition to synthetic fibers including olefins such as polyethylene, polypropylene and the like and polyesters, polyamide and the like, recycled fibers such as rayon, cupra and the like, and natural fibers such as cotton and the like can be used, and nonwoven cloth obtained by appropriate processing methods such as spunlace method, spun-bond method, thermal bond method, melt-blown method, needle punch method and the like can be used. Among these processing methods, the spunlace method provides nonwoven cloth having excellent flexibility and drape property, while nonwoven cloth provided by the thermal bond method is excellent in bulkiness and softness.

The absorbing body 4 interposed between the impermeable back-surface sheet 2 and the permeable front-surface sheet 3 is formed of fluffed pulp and water-absorbing polymer, for example. The water-absorbing polymer in the form of granular powder is mixed into the pulp, for example. The pulp includes chemical pulp obtained from lumber, cellulose fiber such as molten pulp or the like, artificial cellulose fiber such as rayon, acetate or the like, and softwood pulp with a fiber length longer than that of hardwood pulp is preferably used in terms of functions and price.

For the absorbing body 4, synthetic fibers may be used or included. As the synthetic fibers, olefins such as polyethylene, polypropylene and the like, polyesters such as polyethylene terephthalate, polybutylene terephthalate and the like, polyamides such as nylon and copolymers thereof can be used alone or as a mixture of two or more of them. Moreover, complex fibers including core-clad fibers having a fiber with a high melting point as the core and a fiber with a low melting point as the clad, side-by-side fibers, and split-type fibers can be also used. In the case of the above-described synthetic fibers which are hydrophobic, those subjected to surface treatment with a hydrophilic agent are preferably used so as to provide affinity for body fluid.

If the crepe paper 5 surrounding the absorbing body 4 is provided as in this example, the crepe paper 5 is interposed between the permeable front-surface sheet 3 and a back end portion of the absorbing body 4, and the body fluid is quickly diffused by the crepe paper 5 with excellent absorbency, and backflow of the menstrual blood and the like are prevented.

The side nonwoven cloth portions 7 and 7 are provided at both sides on the front surface of the sanitary napkin 1 and extend in the longitudinal direction over substantially the whole length of the napkin 1. Parts of the side nonwoven cloth portions 7 and 7 which extend furthermost to the sides form, together with likewise extending parts of the impermeable back-surface sheet 2, wing-shaped flaps W and W.

For the side nonwoven cloth portions 7, a water-repellent treated nonwoven cloth or hydrophilically treated nonwoven cloth can be used depending on a function to be emphasized. If an emphasis is to be placed on a function to prevent permeation of menstrual blood, vaginal discharge and the like or to improve a feeling on the skin, for example, a water-repellent treated nonwoven cloth coated with silicone, paraffin, alkyl chromic chloride water-repellent or the like is preferably used. If an emphasis is placed on absorbency of menstrual blood or the like in the wing-shaped flaps W and W, synthetic fibers used therefor are preferably swollen, swellable or porous, for example, being copolymers of a noniomer having a hydrophilic group such as an oxidized product of polyethylene glycol, or by including in a manufacturing process of the synthetic fiber, a method of precipitating a hydroxide of metal through treatment with a metal salt such as stannic chloride, or by partial melting of the surface of the synthetic fiber so as to make it porous and from such synthetic fiber making a nonwoven cloth which is hydrophillic on account of the capilarity.

(Emboss Structure)

Figure 2:
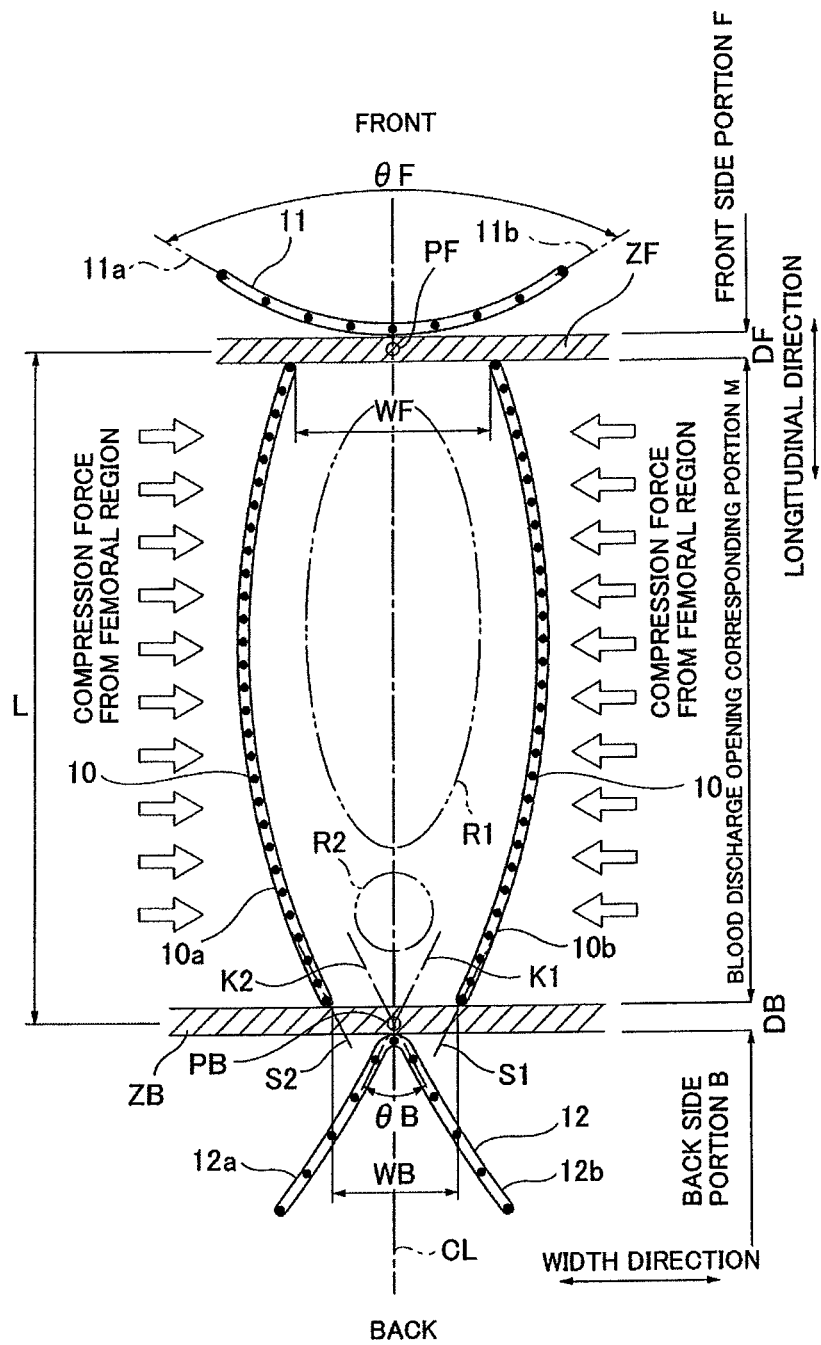
FIG. 2 is an explanatory diagram of embosses.

In the sanitary napkin 1, as illustrated in FIG. 2, embosses 10 to 12 having different shapes adapting to the shape and movement of each part of the body so as to make the sanitary napkin deformable are formed in a portion M of the napkin 1 corresponding to a blood discharge opening portion and a perineal region of a wearer, a front portion F located on the front with a separation width DF provided in the napkin longitudinal direction from the blood discharge opening corresponding portion M, and a back portion B located on the back with a separation width DB provided in the napkin longitudinal direction from the blood discharge opening corresponding portion M, respectively.

A respective blood discharge opening corresponding portion emboss 10 having an arc-shaped curve in the substantially longitudinal direction of the sanitary napkin 1 and having a center of curvature on a center line in the longitudinal direction of the napkin is formed on the blood discharge opening corresponding portion M, each emboss 10 being on a respective side of the longitudinal center line CL, a front side portion emboss 11 in the substantially width direction of the sanitary napkin 1 is formed on the front portion F with separation from the blood discharge opening corresponding portion emboss 10, and a back portion emboss 12 having a substantially inverted V-shape gradually expanding rearward to the both sides from a position (PB) on the longitudinal center line CL is formed on the back portion B with separation from the blood discharge opening corresponding portion emboss 10. Moreover, the pair of right and left blood discharge opening corresponding portion embosses 10 have front end portions and rear end portions provided separately from each other on the both sides of the longitudinal center line, respectively, and a separation width WB between the rear end portions is set smaller than the separation width WF between the front end portions.

As a result, the front in the portion surrounded by the blood discharge opening corresponding portion embosses 10 and 10 is raised to the front surface in a relatively wide range in the width direction by a inward pressure from the both sides in the width direction from the femora in the blood discharge opening corresponding portion M. Therefore, the front suitably fits a blood discharge opening portion R1, while since the back is raised to the front surface side within a relatively narrow range in the width direction, the back suitably fits a perineal region R2. Moreover, the front portion F can easily deform along the curve around the pubes with the front portion emboss 11 as the flexible axis and suitably fits the front of the body. Furthermore, the back portion B can easily deform along the valley of the buttocks with the back portion emboss 12 as the flexible axis and suitably fits the back of the body. As described above, since each of the blood discharge opening corresponding portion M, the front portion F, and the back portion B is deformed along the shape of the body and fits the surface of the body without a gap, wearing comfort and fitting performance are improved, and leakage of menstrual blood or the like is reliably prevented.

In addition, since each portion of the sanitary napkin 1 is deformed along the shape of the body so as to be brought into close contact with the surface of the body and discontinuous zones ZF and ZB of the emboss line where the emboss line is separated in the longitudinal direction are formed in the width direction between the blood discharge opening corresponding portion M and the front portion F as well as the back portion B, respectively, each of the discontinuous zones ZF and ZB functions as a separating zone which prevents movement of the front portion F and the back portion B caused by movement of the body from being interlocked with the blood discharge opening corresponding portion M but separates them from each other, and the fitting performance of the blood discharge opening corresponding portion M to the body is stably maintained regardless of the movements of the front portion F and the back portion B.

Moreover, in this sanitary napkin 1, when the right and left legs are moved back and forth alternately as in walking, the front portion F and the back portion B are interlocked with the movements of the right and left legs and generate a twisting deformation. However, since the center parts in the width direction of the discontinuous zones ZF and ZB function as separation base points PF and PB, respectively, the front portion F and the back portion B are twisted and deformed so as to oscillate around the longitudinal center line CL with the separation base points PF and PB as base ends, respectively. Thus, the movements of the front portion F and the back portion B are not interlocked with the blood discharge opening corresponding portion M, and deformation and wrinkles in the blood discharge opening corresponding portion M can be suppressed.

As illustrated in FIG. 2, in the sanitary napkin 1, in emboss lines 12a and 12b formed on the both sides across the longitudinal center line CL and constituting the back portion emboss 12, the emboss line 12a formed on the left of the longitudinal center line CL is formed such that a virtual line K1 extended to the other side across the longitudinal center line CL toward the front portion becomes substantially parallel with a tangent line S1 of the rear portion of an emboss line 10b formed on the right of the longitudinal center line CL in the blood discharge opening corresponding portion embosses 10. Similarly, the emboss line 12b formed on the right of the longitudinal center line CL is formed such that a virtual line K2 extended toward the front portion to the other side across the longitudinal center line CL becomes substantially parallel with a tangent line S2 of the rear portion of an emboss line 10a formed on the left of the longitudinal center line CL in the blood discharge opening corresponding portion embosses 10. Each of angular differences between the virtual lines K1 and K2 and the tangent lines S1 and S2 is approximately within 10° or preferably within 5°.

Figure 3:
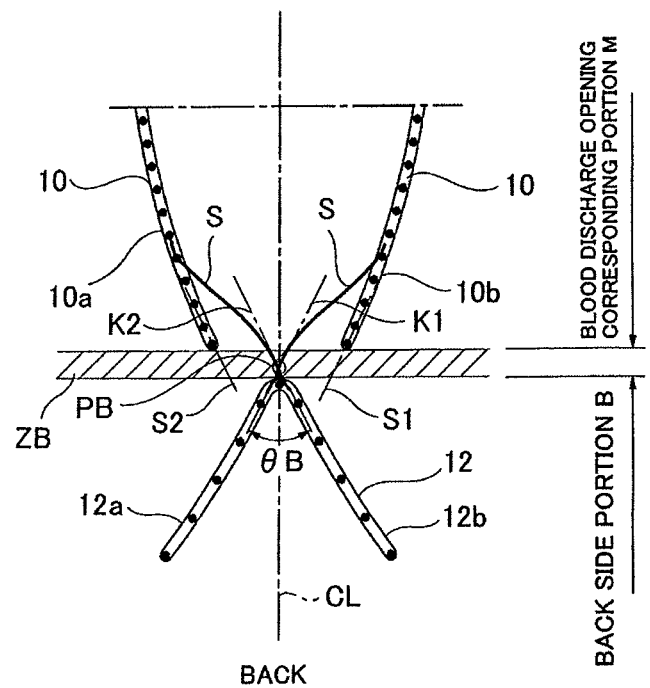
FIG. 3 is an enlarged diagram of the essential part thereof.

In the back portion B where the movement of the body is relatively large, in addition to providing that the separation width WB on the rear portions is smaller than the separation width WF on the front portions of the pair of right and left blood discharge opening corresponding portion embosses 10 and 10 as described above, the virtual lines K1 and K2 and the tangent lines S1 and S2 are formed so that they become substantially parallel, respectively, whereby, as illustrated in FIG. 3, the back portion B is deformed along the valley of the buttocks. As a result, wrinkles S and S having developed in the direction of the tangent line to the blood discharge opening corresponding portion M side beyond the separation base point PB of the back portion emboss 12 can be absorbed by the blood discharge opening corresponding portion embosses 10. Then, wrinkles are no longer formed in the portions surrounded by the blood discharge opening corresponding portion embosses 10 and 10, and the blood discharge opening corresponding portion M can be made to fit the blood discharge opening portion R1 and the perineal region R2 more reliably.

The separation width WF of the front portions of the blood discharge opening corresponding portion embosses 10 and 10 is preferably set to 24 to 35 mm, while the separation width WB of the rear portions is preferably set to 15 to 20 mm.

Figure 4:
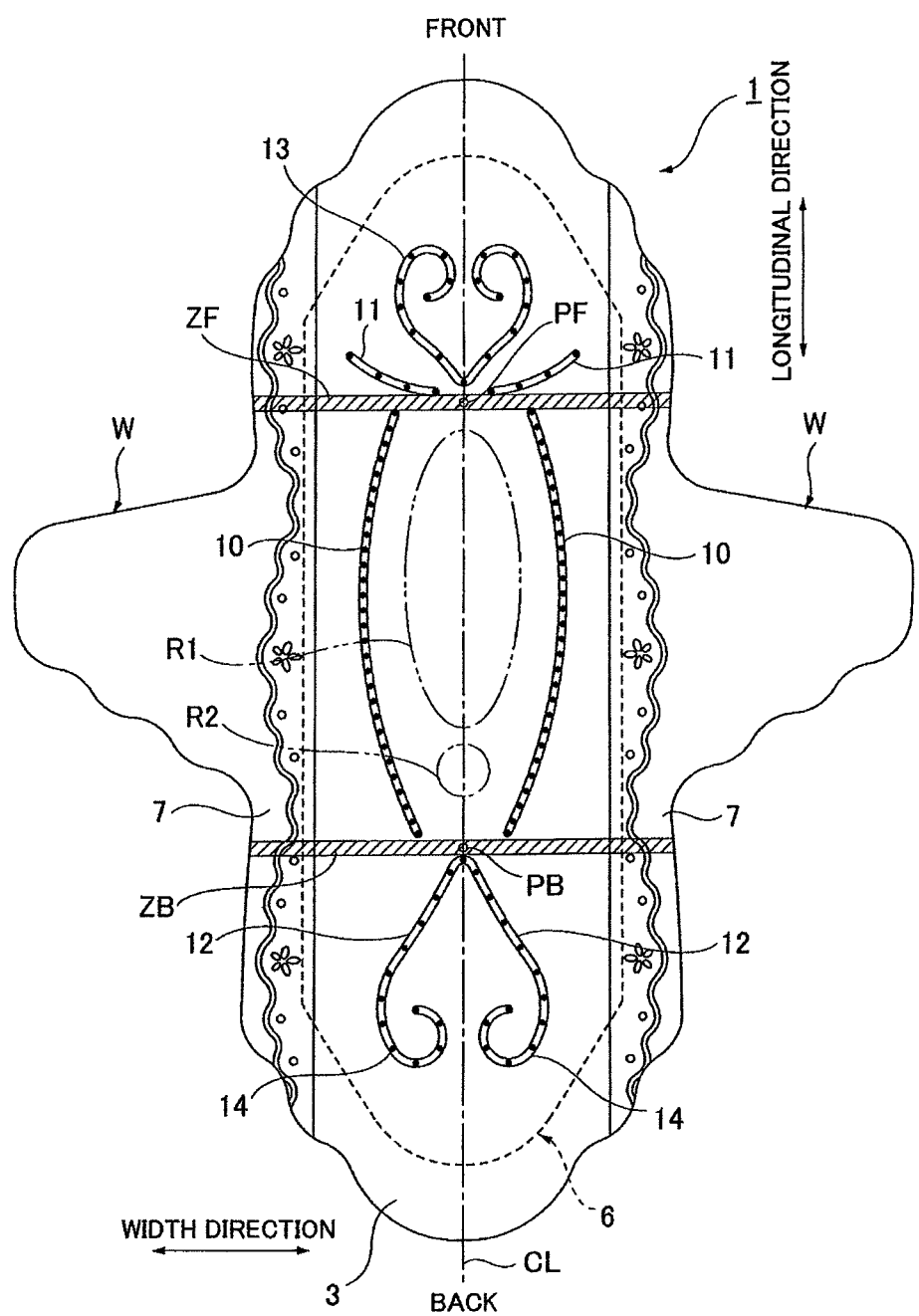
FIG. 4 is an extended diagram of the sanitary napkin 1 according to another embodiment.
Figure 5:
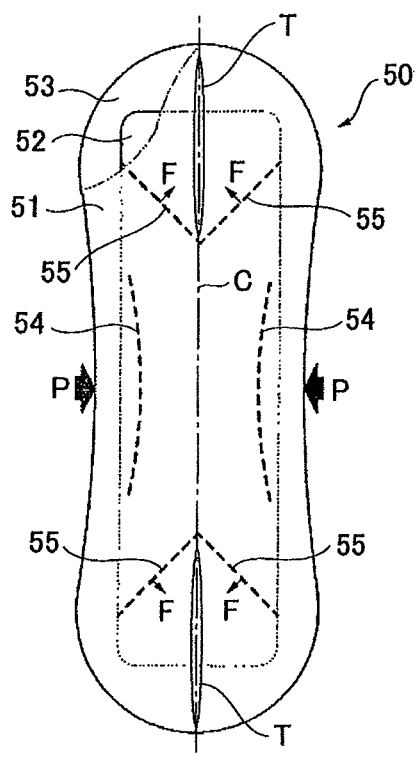
FIG. 5 is an extended diagram of a prior-art sanitary napkin 50.
Figure 6:
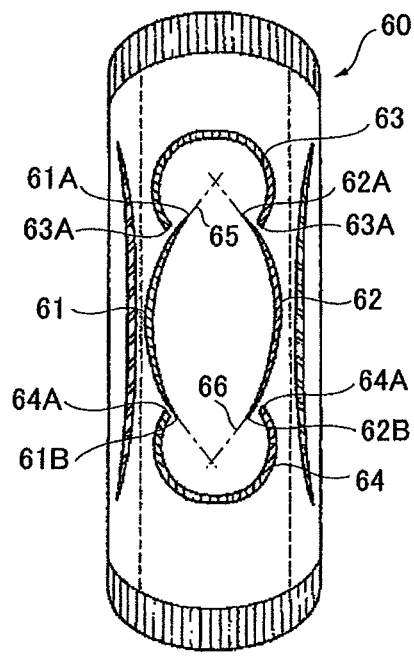
FIG. 6 is an extended diagram of a prior-art sanitary napkin 60.

The front portion emboss 11 is formed by an arc-shaped curve having a center of curvature closer to the front of the sanitary napkin 1 than the front portion emboss 11 itself and having an angle θF formed by the tangent lines 11a and 11b of the respective left and right end portions of the emboss 11 of not less than 90° or preferably 100 to 160°. As a result, the front portion F is made easily deformable with the shape along the curve around the pubes of the wearer due to the front side portion emboss 11 functioning as a flexible axis. The front portion emboss 11 may be divided into plural segments as illustrated in FIG. 4.

The back portion emboss 12 is formed having an angle θB of less than 90° or preferably 60 to 90° formed by the emboss lines 12a and 12b formed on the both sides across the longitudinal center line CL. As a result, the back portion B can be made easily deformable to conform to the shape along the valley of the buttocks of the wearer by the back side portion emboss 12 functioning as a flexible axis. The back portion emboss 12 may be formed linearly on both sides toward the back from the longitudinal center line CL but, as in the illustrated example, it is preferably formed having a gently curved shape with the center of curvature beyond the sanitary napkin 1.

Each of the separation zones ZF and ZB needs to be of some length in the longitudinal direction with the purpose of separation without having the deformation of the front portion F and the back portion B affecting the blood discharge opening corresponding portion M, while if the length is longer than necessary, that prevents fitting to the shape of the body, and the separation zones ZF and ZB become, to the contrary, a source of generating wrinkles. Thus, the length in the longitudinal direction is set to 1 to 10 mm or preferably to 1 to 5 mm. The separation zones ZF and ZB are preferably located at folding line positions for individually packaging the sanitary napkin 1 by folding twice.

The separation zone ZF (separation base point PF) between the blood discharge opening corresponding portion M and the front portion F is preferably located closer to the front end portion of the labia pudenda of the blood discharge opening portion R1, while the separation zone ZB (separation base point PB) between the blood discharge opening corresponding portion M and the back portion B is preferably located closer to the start portion of the valley in the buttocks from the perineal region. As a result, the effect of the fitting performance of each of the parts M, F, and B can be more readily optimized. For this purpose, a distance L between the separation zones ZF and ZB (separation base points PF and PB) is set to 60 to 120 mm or preferably to 80 to 90 mm.

As illustrated in FIG. 4, on the front side of the front portion emboss 11, a design emboss 13 having a shape of a heart expanding to the front and the front end portion thereof being curved inward or the like can be provided with the purpose of distracting from the discomfort and inconvenience of a menstrual period. Moreover, design embosses 14 and 14 continuing from the rear end of the back portion emboss 12 and curved inward can be provided. The design embosses 13 and 14 can conjure an image for a wearer that menstrual blood is stemmed and leakage can be prevented by curving distal end portions inward.

In the illustrated examples, emboss line formation areas are indicated by double lines, and black dotted portions indicate high compression portions and the other portions are low compression portions. An interval between the high compression portions (black dots) is arbitrary.

The invention claimed is:
1. An absorptive article comprising:
an absorbing element interposed between a permeable front-surface sheet and an impermeable back-surface sheet; and
a pair of blood discharge opening corresponding portion embosses each having an arc-shaped curve in a substantially longitudinal direction of the absorptive article and being formed on a portion of the absorptive article which, when worn, corresponds to a blood discharge opening portion and a perineal region of a wearer, each of the embosses being located on a respective side of a longitudinal center line of the absorptive article and having a center of curvature on the opposite side of the center line, a front portion emboss in a substantially width direction of the absorptive article, the front portion emboss being formed on a front portion of the absorptive article with a separation distance provided in the longitudinal direction of the absorptive article from the blood discharge opening corresponding portion embosses, and a back portion emboss having a substantially inverted V-shape gradually expanding rearward to both sides from a position on the longitudinal center line, the back portion emboss being formed on a back portion of the absorptive article with a separation distance provided in the longitudinal direction of the absorptive article from the blood discharge opening corresponding portion embosses, the separation distances respectively separating the front portion emboss and the rear portion emboss from the pair of blood discharge opening corresponding portion embosses so that each of said blood discharge opening corresponding portion embosses are discontinuous relative to the front portion emboss and the rear portion emboss along the longitudinal direction of the article and across the entirety of the width of the absorbing element, the absorptive article being free of embossing therethroughout the separation distances;

the pair of right and left blood discharge opening corresponding portion embosses each have a front end portion and a rear end portion in which each of the front end portions curve toward each other and each of the rear end portions curve toward each other, and a separation width between the rear end portions is smaller than a separation width between the front end portions; and the back portion emboss is formed such that a pair of first and second virtual lines extend from the back portion emboss across the longitudinal center line and toward the front portion of the absorptive article so as to be substantially parallel with a pair of respective first and second tangent lines that extend from the rear end portions of the pair of blood discharge opening corresponding portion embosses, the rear end portions of the pair of blood discharge opening corresponding portion embosses being directed toward the back portion emboss and each of the virtual and tangent lines being inclined relative to the longitudinal center line.

2. The absorptive article according to claim 1, wherein the front portion emboss is formed by an arc-shaped curve having a center of curvature closer to the front of the absorptive article than the front portion emboss itself and an angle formed by tangent lines of both right and left end portions of the arc-shaped curve is at least 90°.

3. The absorptive article according to claim 1 or 2, wherein in the back portion emboss, an angle formed by the embosses formed on the both sides across the longitudinal center line is less than 90°.

* * * * *